Figure 8:
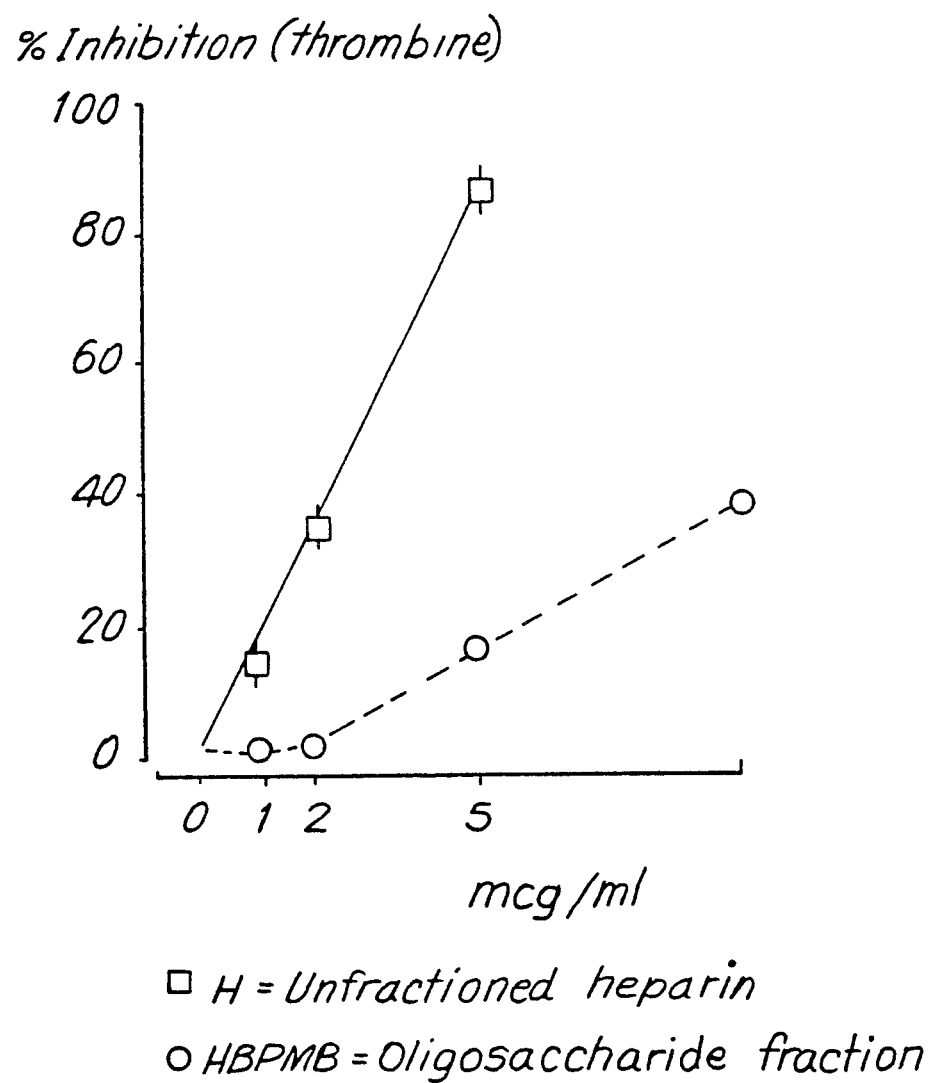
Figure 9:
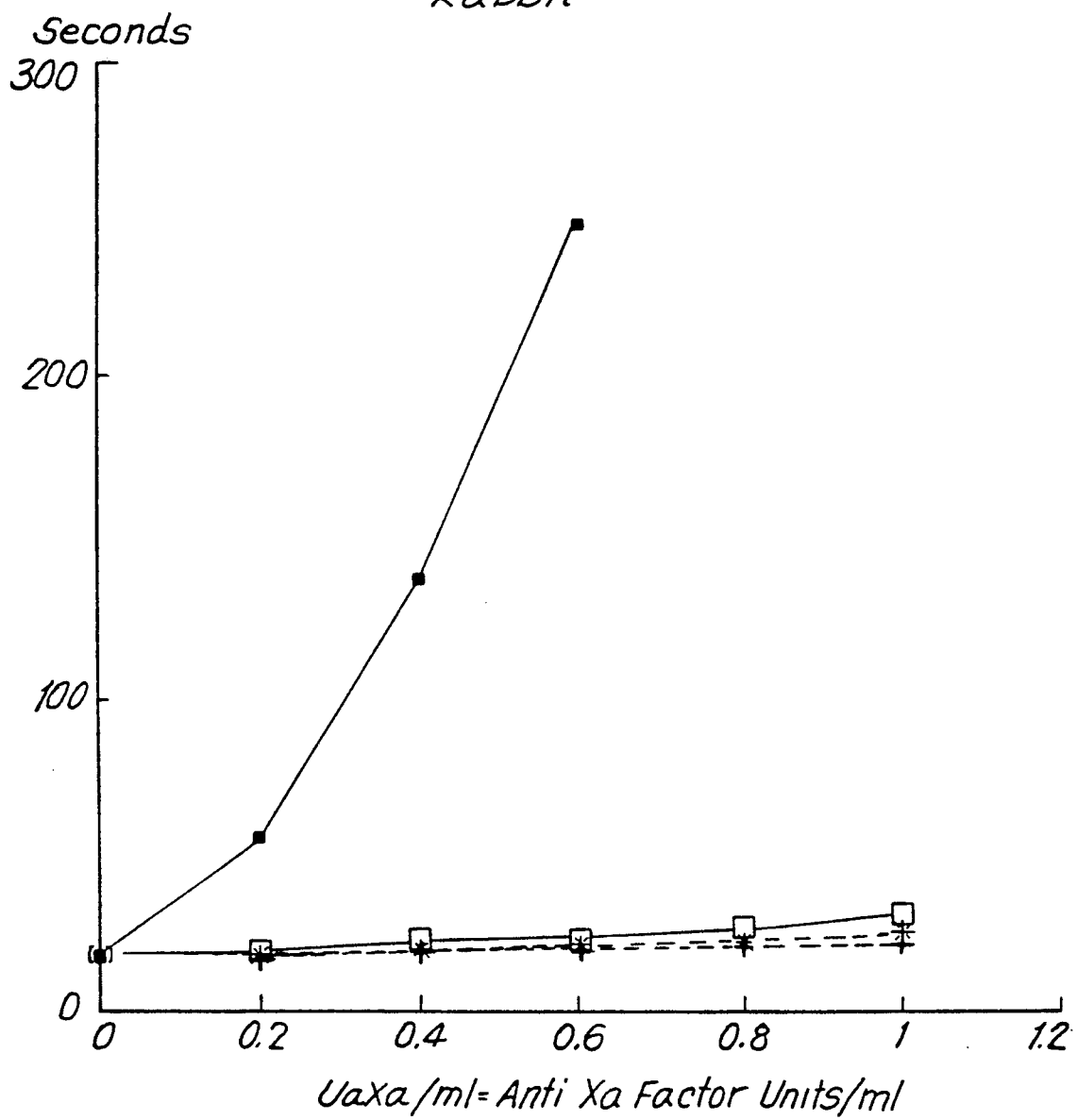
Figure 10:
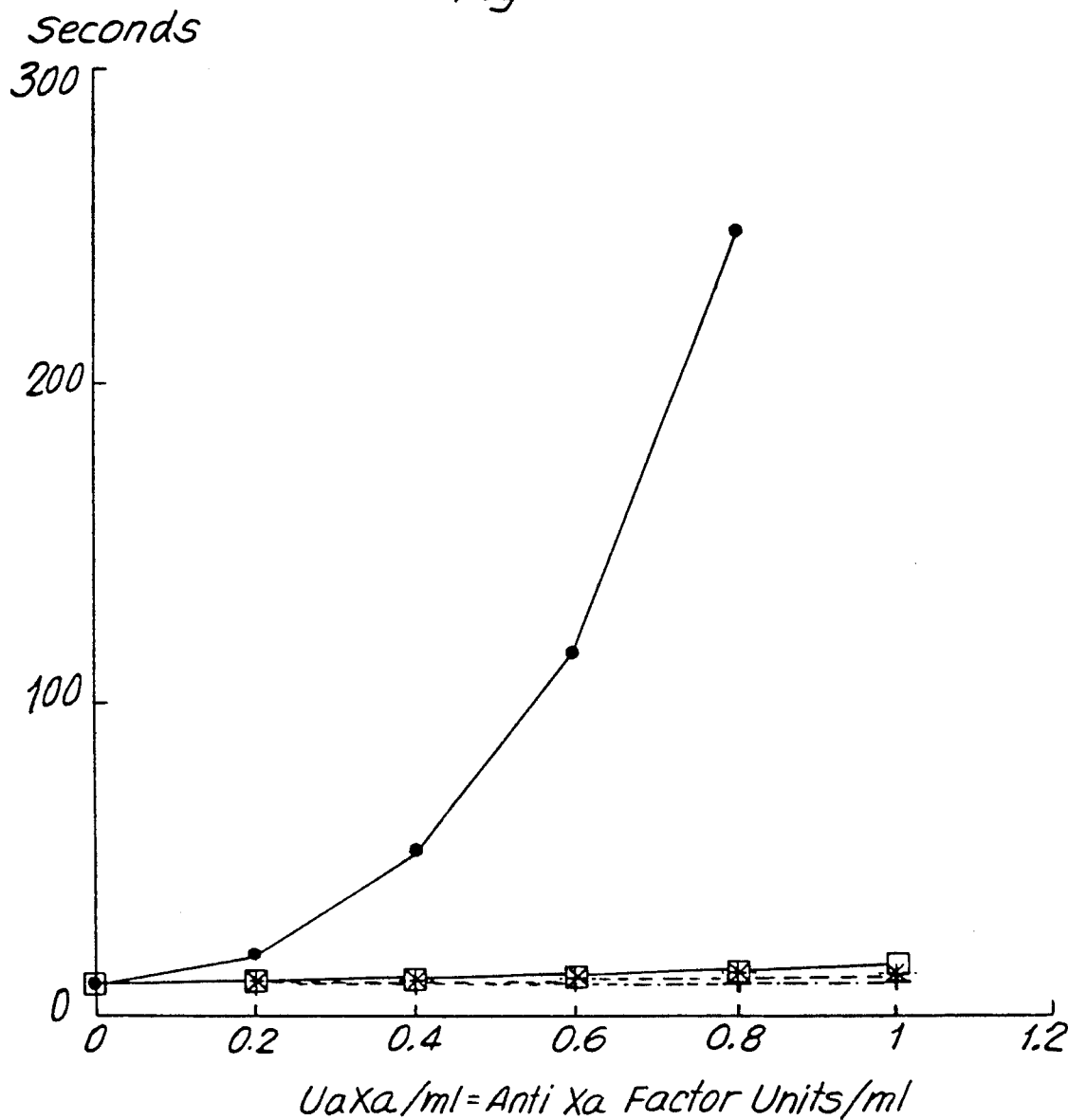

United States Patent [19]
Vila et al.

[11] Patent Number: 5,084,564
[45] Date of Patent: Jan. 28, 1992

[54] PRODUCTION OF OLIGOSACCHARIDE FRACTIONS HAVING ANTITHROMBOTIC PROPERTIES BY CONTROLLED CHEMICAL DEPOLYMERIZATION OF HEPARIN

[75] Inventors: Francisco J. P. Vila, Barcelona; Alberto D. Nusimovich, Andreu de Llavaneres; Pedro T. Gomis, Barcelona, all of Spain

[73] Assignee: Bioiberica, S.A., Palafolls, Spain

[21] Appl. No.: 335,942

[22] Filed: Apr. 10, 1989

[30] Foreign Application Priority Data

Apr. 9, 1988 [ES] Spain ................................. 8801088
Mar. 30, 1989 [ES] Spain ................................. 8901109

[51] Int. Cl.$^5$ ..................... C08B 37/10; A61K 31/725
[52] U.S. Cl. ..................... 536/21.0; 536/127
[58] Field of Search ..................... 514/56; 536/21, 127

[56] References Cited

U.S. PATENT DOCUMENTS

| | | | |
|---|---|---|---|
| 4,303,651 | 12/1981 | Lindahl et al. | 514/56 |
| 4,386,025 | 5/1983 | Jordan | 536/21 |
| 4,438,108 | 3/1984 | Sanders et al. | 514/56 |
| 4,500,519 | 2/1985 | Lormeau et al. | 536/21 |
| 4,745,105 | 5/1988 | Griffin et al. | 514/56 |
| 4,745,108 | 5/1988 | Foley et al. | 514/56 |
| 4,777,161 | 10/1988 | Lormeau et al. | 514/56 |
| 4,791,195 | 12/1988 | Bianchini et al. | 536/21 |

FOREIGN PATENT DOCUMENTS

| | | |
|---|---|---|
| 0098814 | 1/1984 | European Pat. Off. |
| 0121067 | 10/1984 | European Pat. Off. |
| 2945595 | 5/1981 | Fed. Rep. of Germany |
| 3027928 | 9/1981 | Fed. Rep. of Germany |
| 3244214 | 5/1984 | Fed. Rep. of Germany |
| 2482603 | 11/1981 | France |
| 2071127 | 9/1981 | United Kingdom |
| 2131691 | 6/1984 | United Kingdom |
| 8103276 | 11/1981 | World Int. Prop. O. |

OTHER PUBLICATIONS

Hurst et al.; Biochimica et Biophysica Acta 497: 539-547, (1977).
Salzman et al.; J. Clin. Invest. 65: 64-73 (1980).
Thunberg et al.; Carbohydrate Research 100: 393-410 (1982).
Cade et al., Thrombosis Research 35: 613-625 (1984).
Ostergaard et al; Thrombosis Research 45: 739-749 (1987).

*Primary Examiner*—Ronald W. Griffin
*Assistant Examiner*—Nancy S. Carson
*Attorney, Agent, or Firm*—Michael J. Striker

[57] ABSTRACT

The process makes an oligosaccharide fraction from commerically available heparin solutions containing from 1 to 10 % heparin. This oligosaccharide fraction has antithrombotic activity, bioavailability, almost no toxic effects as well as a comparatively lower hemorrhagic risk and a reduction in bleeding time and a molecular weight range of less than 5000 D. This process includes the steps of ultrafiltering an aqueous starting solution of the heparin through a membrane of 3,000 D nominal molecular weight cut-off to form a rejected ultrafiltered heparin solution so that the oligosaccharide fraction does not contain molecular fragments too short for binding with antithrombin and thrombin; performing a phase partitioning of the rejected ultrafiltered heparin solution with aqueous saline solution and dichloromethane and making a heparin-quaternary ammonium complex so as to form a dichloromethane phase and a saline phase so that fractions of a predetermined anionicity and specificity are excluded from the product, adding benzyl chloride to the dichloromethane phase to benzylate and after that adding benzyltrimethylammonium hydroxide to the dichloromethane phase to form a depolymerized heparin fraction in the dichlormethane phase and subsequently isolating the oligosaccharide fraction by steps including phase partitioning to form other saline phases, debenzylating, adding sodium hydroxide to the other saline phases and subsequently lyophilizing and dialyzing. The oligosaccharide fraction formed by this process with the above-mentioned properties is also a part of the invention.

8 Claims, 11 Drawing Sheets

Figure 11:
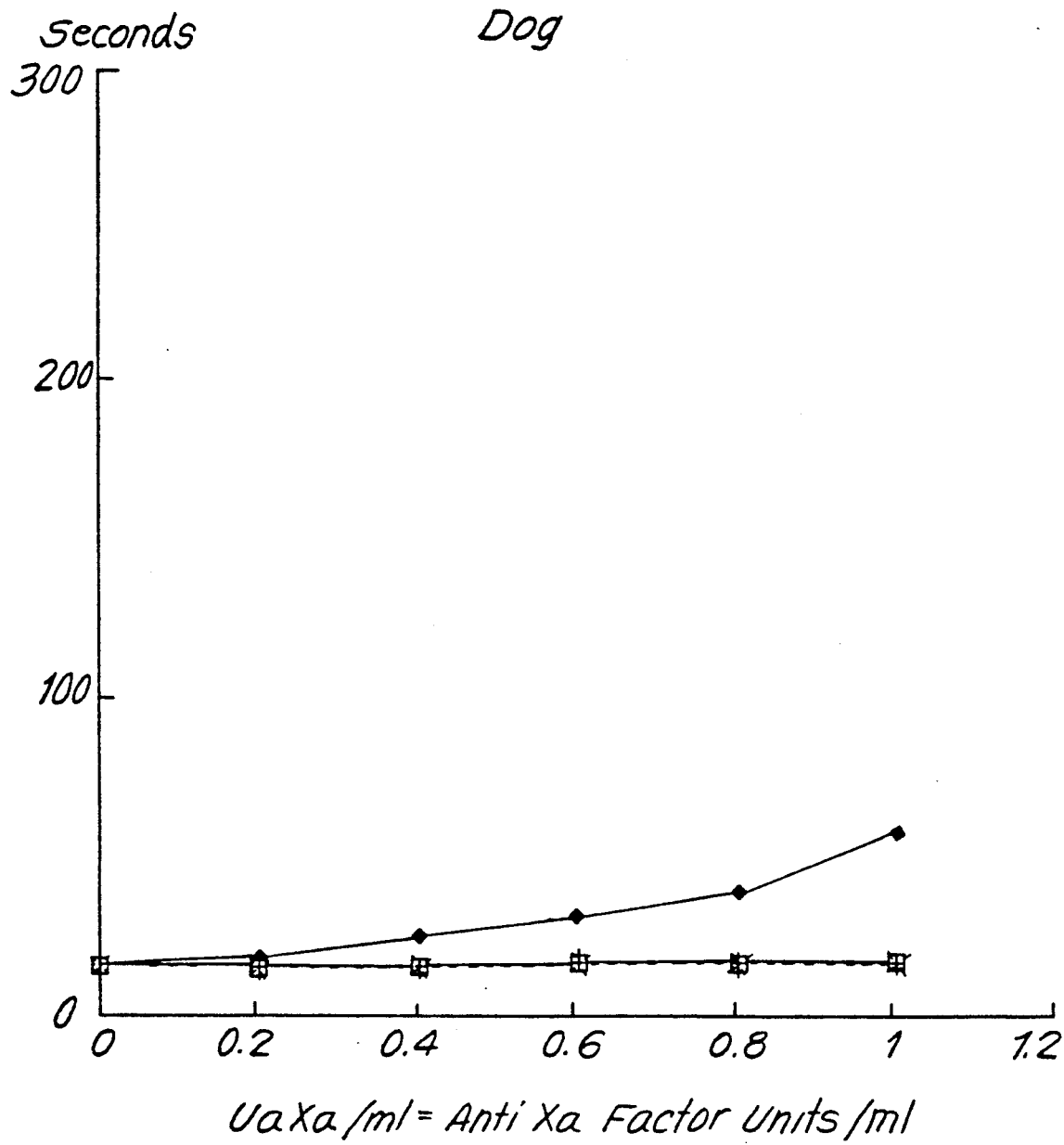
Figure 12:
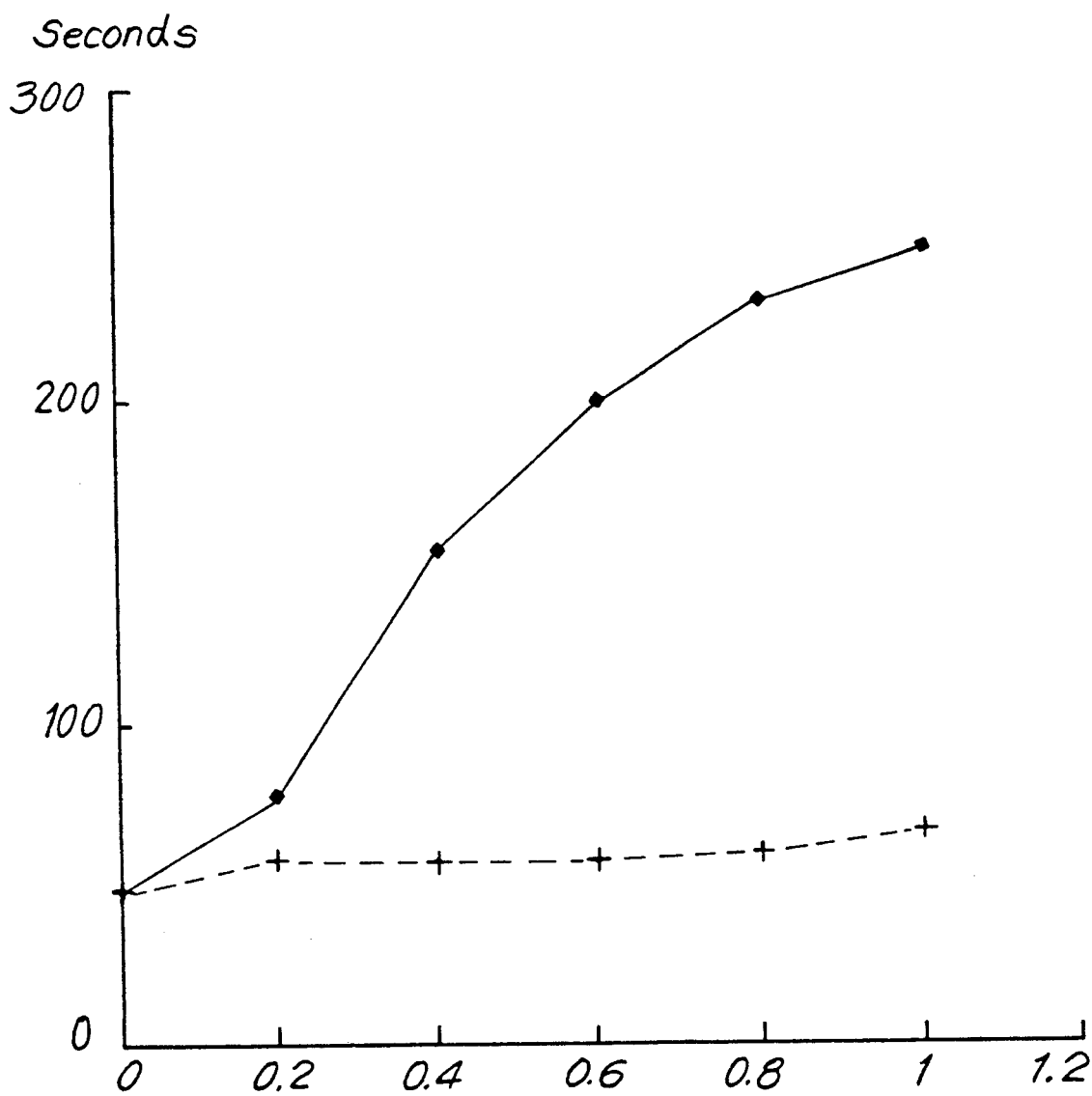
Figure 13:
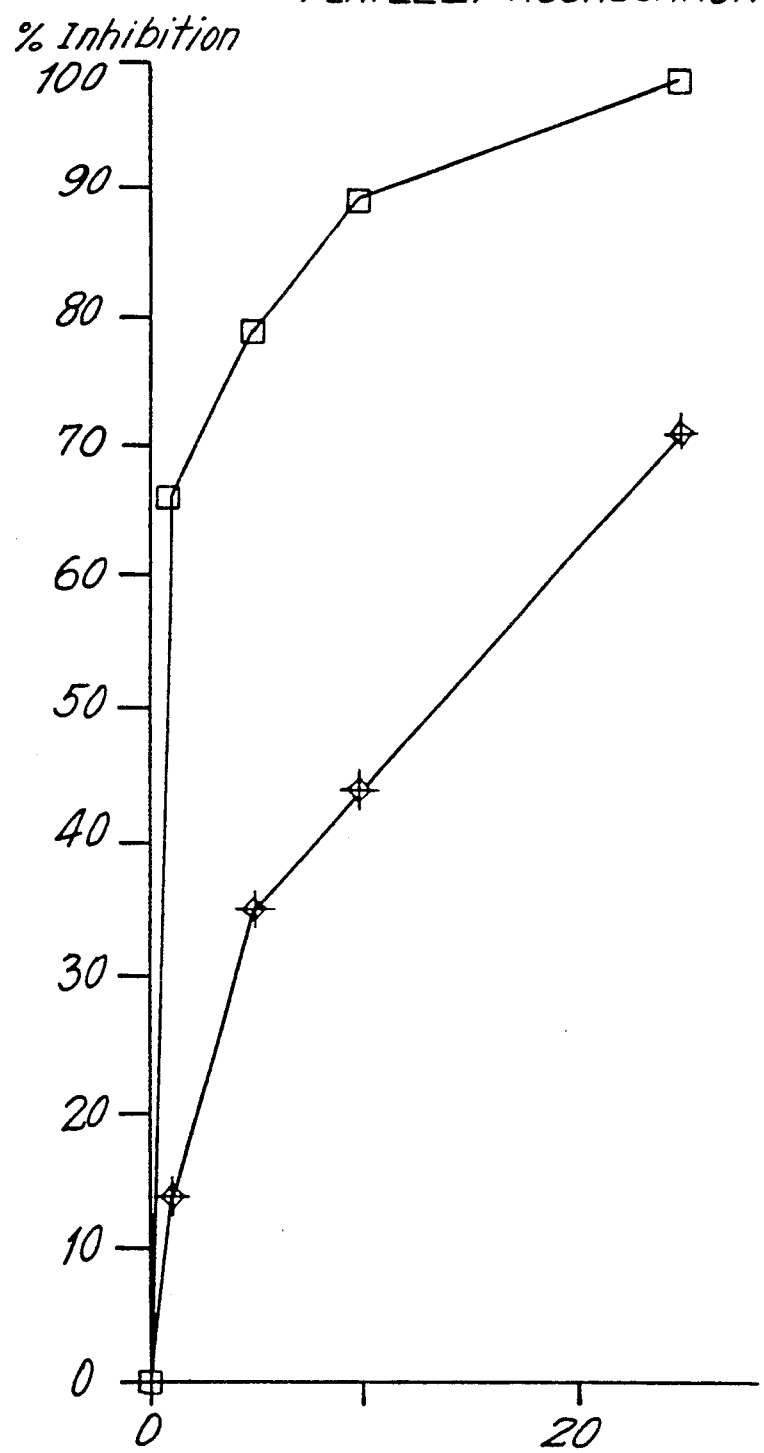

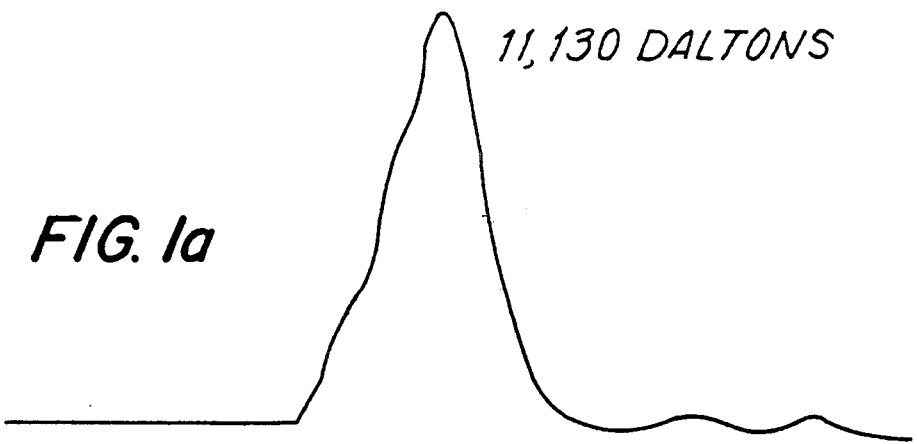
FIG. 1a    11,130 DALTONS
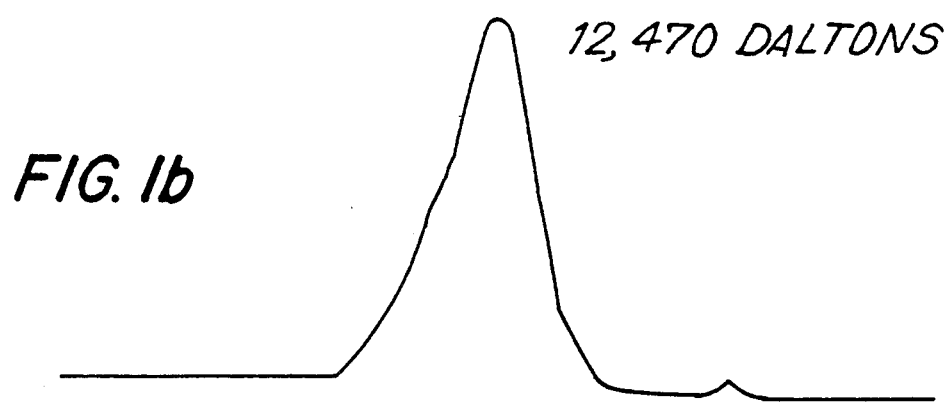
FIG. 1b    12,470 DALTONS
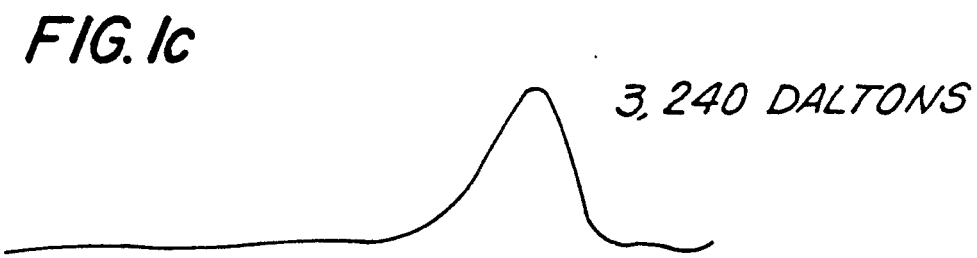
FIG. 1c    3,240 DALTONS

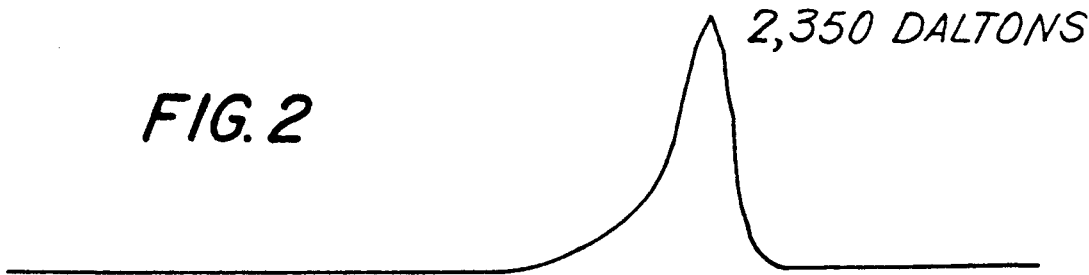
FIG. 2  2,350 DALTONS
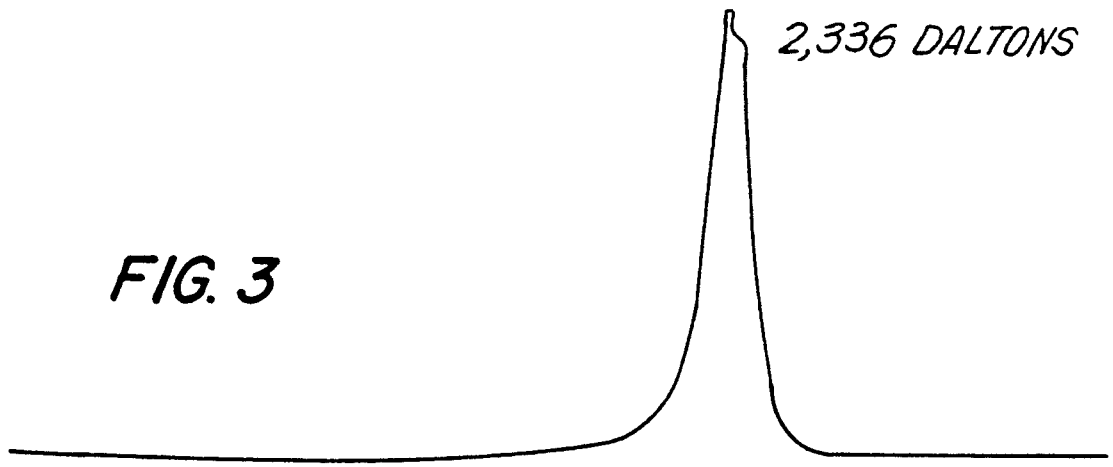
FIG. 3  2,336 DALTONS
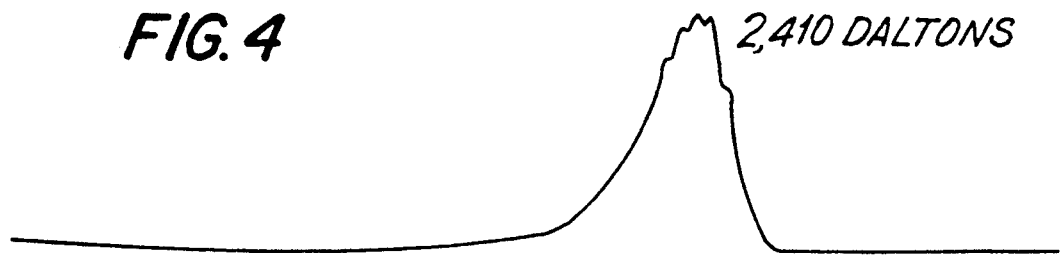
FIG. 4  2,410 DALTONS

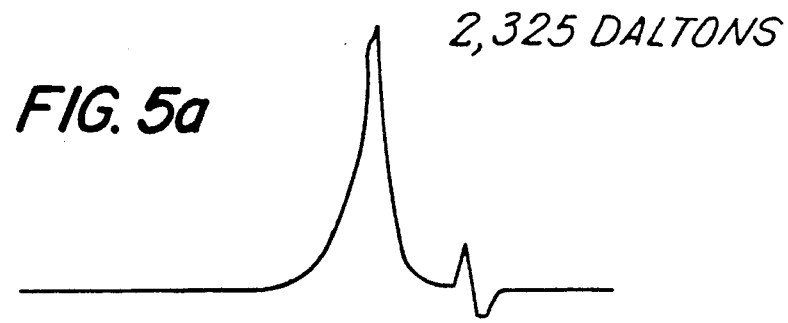
FIG. 5a  2,325 DALTONS
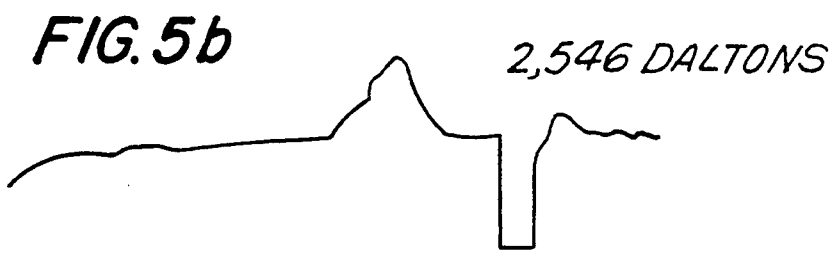
FIG. 5b  2,546 DALTONS
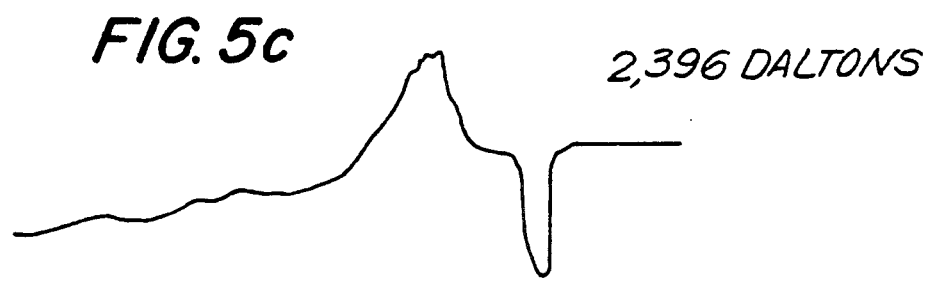
FIG. 5c  2,396 DALTONS

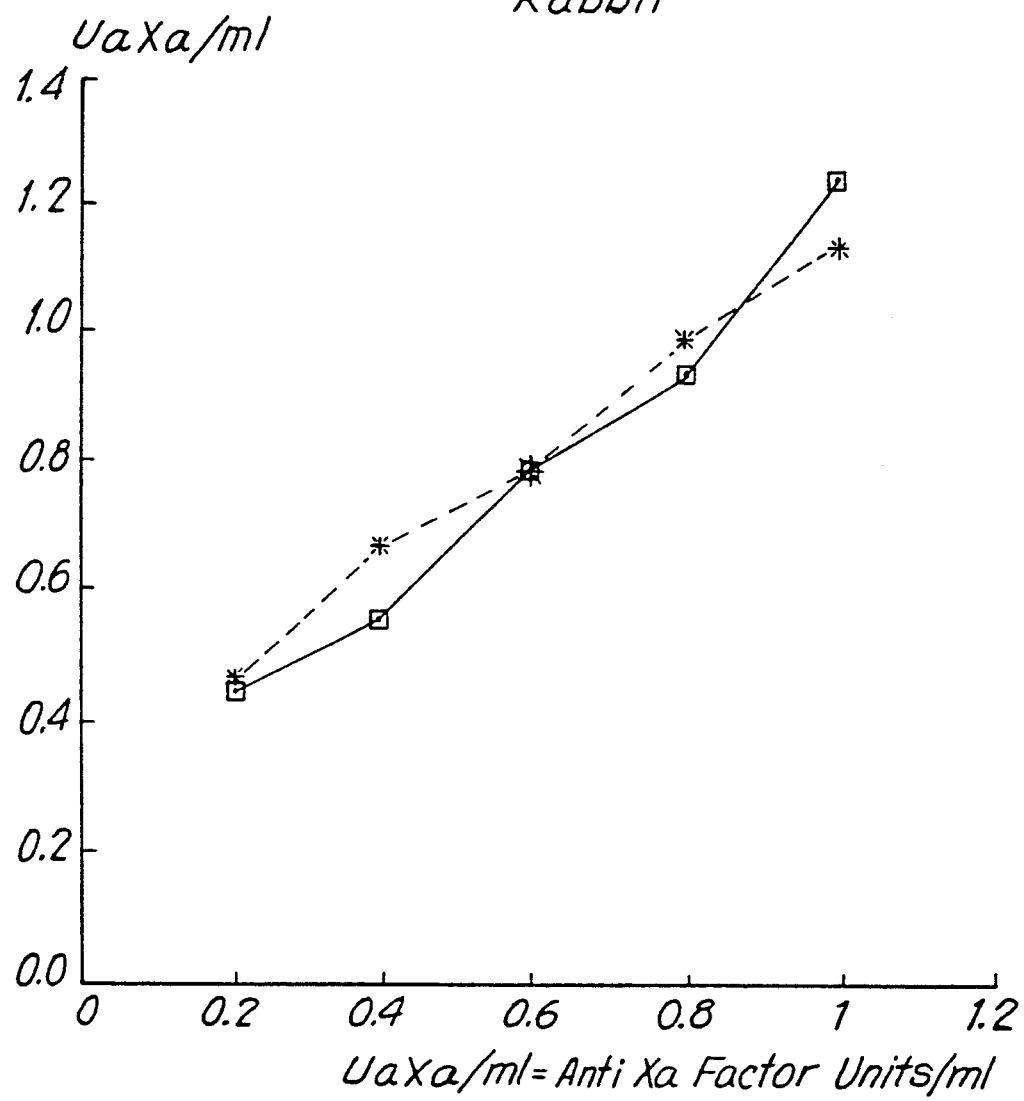

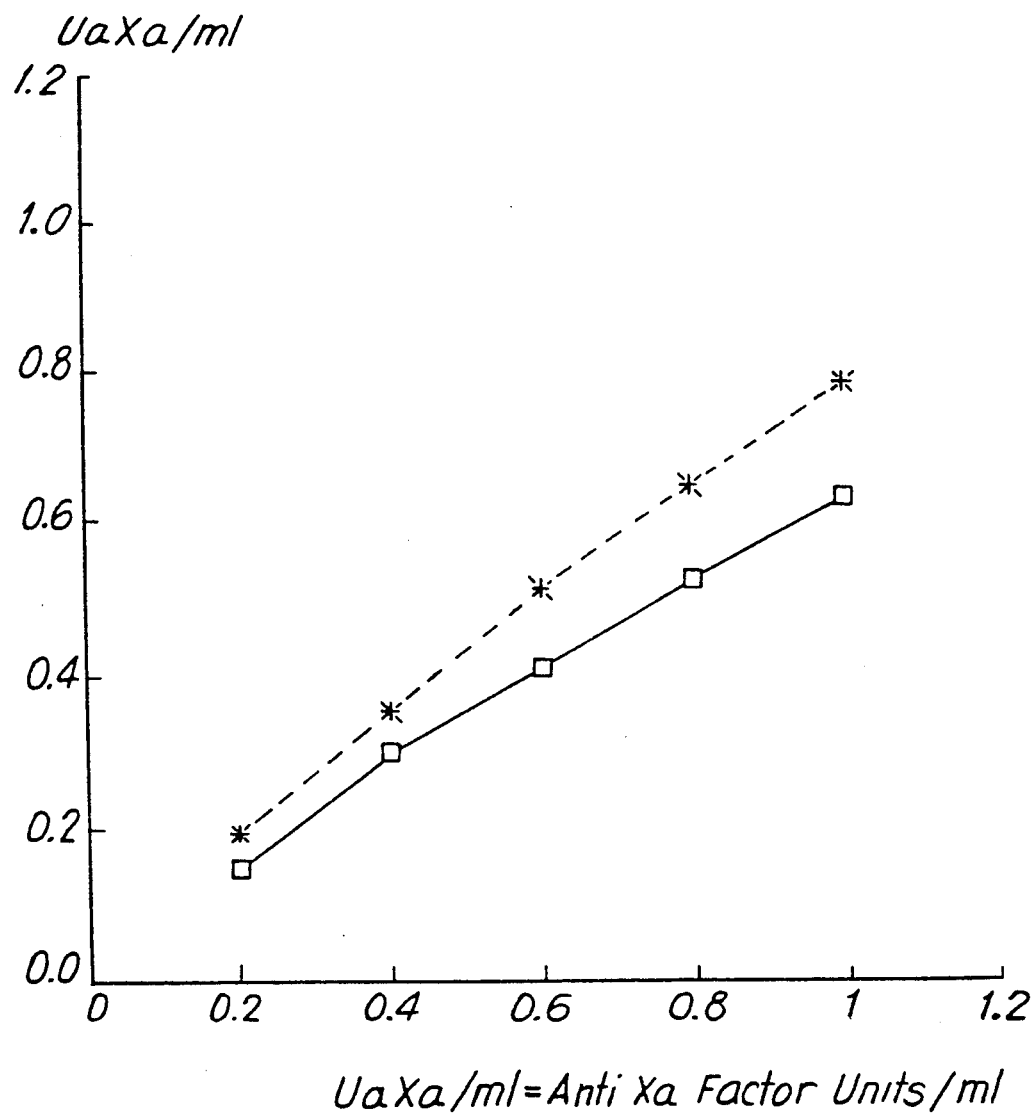

ACTIVATED PARTIAL THROMBOPLASTINE TIME
APTT
Rabbit

UaXa/ml = Anti Xa Factor Units/ml

• H = Unfractioned heparin
+ HBPMB = Oligosaccharide fraction

PLATELET AGGREGATION

□ H = Unfractioned heparin
✥ HBPMB = Oligosaccharide fraction

PRODUCTION OF OLIGOSACCHARIDE FRACTIONS HAVING ANTITHROMBOTIC PROPERTIES BY CONTROLLED CHEMICAL DEPOLYMERIZATION OF HEPARIN

This invention relates to a physico-chemical process for manufacturing oligosaccharide fractions from commercial heparin having useful pharmaceutical properties, such as: high inhibition of the Xa factor, high antithrombotic, and low anticoagulant activity.

Heparin is a polydisperse polymer of the glycosaminoglycan family. Commercial products obtained from different sources (pork and beef mucose and bovine lungs) contain a mixture of polysaccharides with a continuous distribution of molecular weight in the range of 1500 to 30000 Daltons. Nader, H. B. et al. *Biochem Biophys. Res. Commun.* 57, 448–493 (1974).

Heparin produces a high anticoagulant action increasing the inhibitory effect of antithrombin III (AT III) in various activated factors of the coagulation cascade. This action is influenced by its molecular weight profile. It is verified that decreasing the molecular weight causes an increase in the ratio between the anti-Xa and antithrombotic activity.

It is known (Andersson L. et al. Trombos. Res. 9, 575–583, (1976) Barrowcliffe T. W. et al. Thrombos. Res. 12 27–36 (1978), Lane D. A. et al. Trhombos Res. 12 257–271, (1978), that by fractioning the commercial heparin of distinct origins in gells such as sephadex or ultragel Ac. 44, different mean molecular weight fractions are obtained of a definite range which demonstrates an alteration in the anticoagulant activity according to methods such as USP XXI, BP or APTT and which are relatively more active aginst the Xa factor than the thrombin (Bjork etc.)

The essential pentasaccharidic sequence corresponding to the active site of binding between the heparin and the antithrombin is also well-known. The molecular weight fractions lower than 5000 Daltons (16–18 monosaccharides) which still contain this sequence are not long enough for simultaneous binding with the antithrombin and thrombin and can therefore, only neutralize the Xa factor.

Heparin's hemorrhagic risk which is more related to the platelet aggregation than to coagulation, is reduced with the low molecular weight fractions of heparin. (Westwick J. et al. Thrombos Res. 42, 435–447 (1986), Salzman, E. W. et al. *J. Clin. Invest* 65 64–73 (1980) have proved that low molecular weight fractions with high affinity for the AtIII (Antithrombine III) interact with platelets less than high molecular weight heparin fractions with high affinity to ATIII. Cade, N. F. et al. Thrombos Res. 35, 613–625 (1984) have demonstrated the lower inhibition effect of the low molecular weight heparins on the platelets' functions. Studies of Ostergaard, P. B. et al. Thrombos Res. 45, 739 (1987) have demonstrated that the doses of low molecular weight heparin necessary for preventing the formation of thrombos in animals are below the hemorrhagic risk level. Consequently the retention of the antithrombotic properties of Heparin, reducing the hemorrhagic risk, are highly interesting. In this connection, various processes of degrading heparin with chemical reagents or enzymatic agents are described in the literature. These processes, commonly known as depolymerization, have the objective of obtaining fragments with a mean molecular weight lower than the heparin used as raw material and preserving its polysaccharidic structure. Amongst these processes, those based on nitrous acid can be quoted, where the consequent fragments are characterized by a terminal residue consisting of 2-5 anhydromanose.

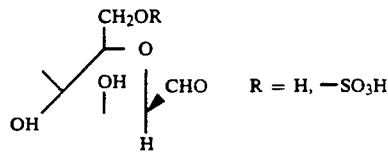

(U.S. Pat. No. 4,438,261, WO 82/03627; Eur. Patent Appl. No. 0048231). Others are based on depolymerization in a sulfuric acid medium with a subsequent resulfonation with a chlorosulfonic acid mixture (Nagasaka K. et al. Archiv Biochem, Biophys 150, 451 (1972). French Patent Appl. No. 2,538,404) or by peroxide or peracid action in presence of metalic catalysts (WO 86/06729) or by B-elimination in an alkaline medium of alkyl or allyl esters of heparin (Eur. Patent Appl. No. 0040144) resulting in the obtention of oligomers with a mean molecular weight of 2000 to 9000 Daltons possessing an unsaturated terminal group as follows

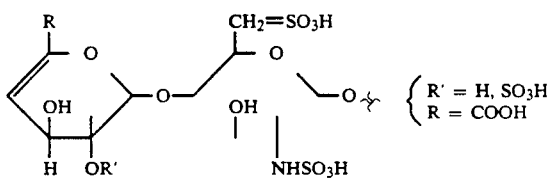

The yield of this process is low, considering the precipitation of the depolymerized product in an aqueous or organic medium and, in cases where the final product is lyophylized before elimination of the non-desired subproducts, the range of the molecular weight distribution is enlarged due to the inclusion of very low molecular weight fractions. A further process consisting of the enzymatic depolymerization with heparinase (Eur Patent Appl. No. 0064452; B. Biol. Chem. 257 7310 (1982) is effected with diluted solutions with low yields.

SUMMARY OF THE INVENTION

It is an object of the present invention to provide an improved method of making an oligosaccharide fraction from commercially-available heparing having improved antithrombotic activity and bioavailability and almost no toxic effects, this method having an improved yield of an oligosaccharide fraction having a molecular weight range of less than 5000 D.

The process described in this invention has the following characteristics:

(a) The initial partition of the raw material by ultrafiltration (commercial heparin) with the object of not submitting the molecular weight heparin fraction lower than 3000 Daltons to depolymerization in order to avoid the presence of fragments of 10–16 saccharides or less in the final product. Despite the demonstrated necessity of the existence of a specific pentasaccharidic sequence which binds the antithrombin III (ATIII), Thunberg L. et al. *Carbohydr. Res.* 100, 393–410 (1982), Petitou, M. *Nouv. Rev. Fr. Hematol* 26, 221-231 (1984), the decasaccharide or pentasaccharide fragments inhibit the Xa factor in the presence of V/Ca++/Phospholipid Complex less than the eikosaccharides. Barrowcliffe, T. W. et al. *Biochem J.* 243, 31-37 (1987).

(b) Continuous operation in liquid phases without intermediate insulation, reduces the loss associated with precipitation and filtration.

(c) Elimination, prior to depolymerization, by phase partition, of low anionicity heparin fractions which, if included, would provide low or null specificity for the antithrombin (ATIII). Hurst R. E. et al. *Biochim, Biophys Acta,* 497, 539-547 (1977) have studied the partition of polyanionic glycosaminoglycan complexes with quaternary ammonium cations between alcoholic liquid phases and inorganic salt aqueous solutions. In the present invention, partition is performed between an aqueous saline solution and dichloromethane solution, the latter solvent being used for carrying the heparin in its esterifying, depolymerizing and molecular weight partition steps.

(d) Depolymerization effected in various cycles with the object of obtaining with a high yield a product with a defined molecular weight range lower than 5000 Daltons and a previously selected mean molecular weight.

As indicated, the B-elimination, by the action of a base on the esterified carboxyl group of heparin is one of the depolymerizing chemical methods used. Up to the present, this has been used in the aqueous or organic phase, isolating the ester and consequently reacting the base on the ester in one stage only. In order to obtain the mean molecular weight desired, other authors have studied the esterification grade control, the elimination time and the base's concentration. Before this invention, the results were a dispersion of molecular weights above 8000 Daltons which, in cases of mean molecular weights of 3000-5000 Daltons, represents a high contribution of extreme molecular weight fractions in the final product or the inclusion of a further fractionation stage subsequent to the depolymerization with the consequent reduction in yields.

The process according to our invention is applied to aqueous solutions of commercial heparin at a 1 to 10% concentration (more specifically 5%). The first stage consists in the ultrafiltration of this solution through a hollow fiber cartridge H10 P3-2025 AMICON of 3000 NMWL in order to eliminate molecular weight fractions lower than 3000 Daltons. FIG. Ia shows the molecular weight distribution curve of the initial heparin, FIG. Ib the rejection of 3000 and FIG. Ic permeation.

Although heparin is insoluble in organic solvents, its complexes with quaternary ammonium cations such as arylalkylammoniums are, under certain conditions, soluble in dichloromethane. These complexes have been proved susceptible of partition between aqueous solution of an electrolyte and dichloromethane, the partition coefficient being a function of the electrolyte used and its concentration. Partition is sensitive to the anionic nature of the glycosaminoglycan and, therefore, allows an adequate segregation of the low anionicity heparin fraction. Consequently, the rejection of the ultrafiltration with the hollow fiber cartridge, consisting of an aqueous solution of heparin is submitted to the addition of sodium chloride up to a concentration of 0.17M and a volume equal to 5% of the solution treated, of a Benzethonium chloride solution at 7.5% in dichloromethane, and equilibrated with a 0.17M solution of sodium chloride in water. Most of the heparin passes to the dichloromethane (SI) with the formation of a heparin-quaternary ammonium complex and the separation of a low anionicity fraction in the saline aqueous phase (SII) (lower sulfate: uronic acid ratio) is verified.

Once the (SI) dichloromethane phase containing the heparin-quaternary ammonium is separated, the benzylic ester of the heparin's carboxylic acid is obtained by adding Benzyl Chloride to the (SI) solution (4-8 hours, 20°-25° C.).

The organic base, Benzyltrimethylammonium Hydroxide is subsequently added without isolation of the ester to the benzylated complex at room temperature (20°-25° C.) and the reaction proceeds for 2-4 hours. The depolymerization reaction is interrupted by the addition of 1N/hydrochloric acid.

The depolymerized heparin fraction is separated from the nondepolymerized by phase partition between the solution in dichloromethane and an aqueous solution of sodium 0.07M-0.12N chloride, previously equilibrated with dichloromethane.

The depolymerized benzyl heparinate contained in the aqueous/saline solution (SIII) is debenzylated by treatment with 1N to 2N sodium hydroxide at a low temperature (0°-5° C.) for 1 to 4 hours.

The dichloromethane solution (SIV) containing the benzyl heparinate complexed with quaternary ammonium is once again treated with the organic base (HB).

Rupture of the quaternary ammonium complex is effected by partition of phases between the dichloromethane solution and a 1.2M sodium chloride solution. The passage of all the depolymerized benzylated heparin to the saline aqueous phase (SV) is verified.

The saline aqueous solutions of the depolymerized heparin from the debenzylation step are dialyzed by ultrafiltration in 1000NMW membranes and lyophylized.

The oligosaccharides resulting from the present depolymerization process can also be isolated from the aqueous solution of the dialysis by precipitation with nonaqueous solvents such as methanol, ethanol or acetone essentially in their sodium salt form.

The oligosaccharides of the present invention can also be salified with lithium, potassium, calcium or magnesium by the usual process, consisting in releasing the corresponding heparinic acid by means of an interchangeable cationic resin in proton form and subsequent salification of the heparinic acid with the desired cation.

The oligosaccharides of this invention have the following formula:

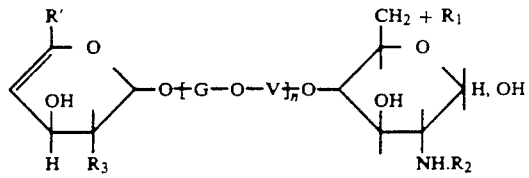

The double bond between C4 and C5 resulting from the B-elimination may or may not exist, depending on whether the product after debenzylation and dialysis, is treated with alkaline permanganate or sodium borohydride.

R' represents a hydrogen atom or a carboxyl group in free or salified form. R1 represents an hydroxyl or sulfate group in acid or salified form. R2 designs a sulfonated group in acid or salified form or an acetyl group. R3 designs an hydroxyl or sulfate group in acid or salified form. —O— designs an oxygen bridge. G represents glucosamine chains and U uronic acid chains (glucuronic acid, L-iduronic acid and sulfated L-iduronic acid) according to their presence in the original heparin's polysaccharidic structure.

The oligosaccharides in this invention have the following characteristicas as sodium salts:
Uronic Acid content: 25-40%
Sulfur content: 10-13%
Nitrogen content: 1.8-2.5%
Specific rotary power in aqueous solution at 20° C.
  $(\alpha)_D^{20}$: $+28°+55°$
Mean molecular weight: 3000-7000 D.

According to the mean molecular weights and range of same obtained from application of this process, the final products can be classified as follows:

| Mean molecular weight | 1500-3000 D. | 3000-5000 D. | 5000-7000 D. |
|---|---|---|---|
| Anticoagulant activity in vitro USP XXI | 10-50 | 50-70 | 70-120 |
| AntiXa activity in vitro | 90-160 | 90-180 | 120-180 |
| APTT activity in vitro | 10-40 | 30-60 | 60-110 |
| AnitXa activity in vitro APTT activity in vitro | 4-10 | 2-6 | 1.5-3 |

The following examples demonstrate the invention without limiting its scope.

EXAMPLES

EXAMPLE I

A commercial heparin originating from hog mucosa with the following features was used:
Anticoagulant activity USP XXI (Std. WHO IV): U/mg.
Uronic acid content: 31.6% o.d.b.
Sulfur content: 11.8% o.d.b.
Nitrogen content: 2.1% o.d.b.
Specific rotary powder in aqueous solution at 20° C.
  $(\alpha)_D^{20}$: $+47.4°$
Mean molecular weight (see FIG. 1a): 17,000 Daltons
300 gr. of Sodium Heparin are dissolved in 12 liters of distilled water. The solution is concentrated to half its original volume by ultrafiltration through membrane AMICON E-10 P3-2025 and dialyzed with two volumes of distilled water by the same equipment. 59.7 gr. of Sodium Chloride and 300 ml of a solution of Benzetonium Chloride at 7.5% in Dichloromethane is added to the rejection obtained from this last operation. The solution obtained is extracted with 6.5 lts of a 7.5% Bencetonium Chloride solution in Dichloromethane which, has been previously equilibrated with an aqueous solution 0.17M in Sodium Chloride. The phase are separated by extraction or centrifuging and the dichloromethane phase is transferred to a jacketed reactor provided with a stirrer and stirred gently with 300 ml of pure benzyl chloride at a temperature of 20° to 25° C. The stirring is maintained during 6 hours at the same temperature, after which 60 ml of Benzyltrimethylammonium Hydroxide are added and the stirring continued 3 further hours. Subsequently 10 ml of 1N hydrochloric acid are added and this solution is extracted with 6 lts of a 0.1M Sodium Chloride aqueous solution.

400 ml of 2M NaOH are added to the saline solution and stirred during 2 hours at 4° C., neutralized with 1N HCl and then dialyzed with an ultrafiltration unit equipped with a membrane of 1000 D. Molecular weight cut-off.

The dichloromethane solution from the phase partition with the sodium chloride 0.1N solution is recycled in the reactor and 60 ml of Benzyltrimetylammonium Hydroxide are added and maintained in agitation during 3 hours at 20° to 25° C. 10 ml of 1N hydrochloric acid are then added and the solution is extracted with 6 lts of an aqueous sodium chloride 2M solution.

400 ml of 2M sodium hydroxide are added to the aqueous saline solution containing the benzyl heparinate and the solution is maintained in agitation during 2 hours at 2° C., then neutralized with 1M hydrochloric acid and dialyzed with an ultrafiltration membrane of 1000 NMW cut-off, until the chlorides are eliminated. The rejected solution is lyophilized (P2). P1 and P2 are blended and 254 gr of product are obtained with the following characteristics:

Mean molecular weight: 4700
Weight average molecular weight (MW): 5600
Number average molecular weight (MN): 3800
Anticoagulant activity (USP XXI): 53 U/mg.
AntiXa activity: 163 U/mg.
APTT Activity (Teien A. et al. Thromb. Res. 11, 107 (1947): 44 U/mg.
Polydispersion Q=MW/MN: 1.47
(See FIG. II)

EXAMPLE II

The raw heparin used was the same sodium heparin as in Ex,I.

300 gr of sodium heparin are dissolved in 12 lts of distilled water. The solution is concentrated to half its original volume by ultrafiltration with an AMICON H-10 P3-2025 membrane and dialyzed with two volumes of distilled water with the same equipment, obtaining a rejection of 6 lts, to which 59.7 gr of sodium chloride are added. The phases are separated by extraction or centrifuging and the dichloromethane (SI) transferred to a jacketed reactor with an agitator. 300 ml of pure benzyl chloride are added and stirred gently at a temperature of 20° to 25° C. Agitation is maintained during 6 hours at this temperature, after which 60 ml of Benzyltrimethylammonium are added continuing agitation 4 further hours at the same temperature. 10 ml of 1N Hydrochloric acid are then added and the solution is extracted with 6 lts of a 0.07M sodium chloride aqueous solution. 400 ml of 2N NaOH are added to the saline aqueous solution and agitation is maintained during 2 hours at 4° C., after which the solution is neutralized with 1M HCl and dialyzed with an ultrafiltration membrane of 1000 NMW cut-off. The product is lyophilized (P1) and the dichloromethane solution from the partition phase with the 0.7M sodium chloride is recycled, 60 ml of benzyl chloride added and gentle agitation maintained during 6 hours at 20° to 25° C. 20 ml of 1M hydrochloric acid are then added and the solution is extracted with 6 lts of a 2M sodium chloride aqueous solution.

To the saline aqueous solution containing the benzyl heparinate, 100 ml of 2N sodium hydroxide are added and agitation continued during 2 further hours at 4° C., after which the solution is neutralized with 1N hydrochloric acid and dialyzed with an ultrafiltration membrane of 1000 NMW cut-off until the chlorides are eliminated.

The rejected solution is lyophylized (P2) and blended with P1, obtaining 228 gr of product with the following characteristics:
Mean molecular weight: 2900
Average molecular weight (MW): 3600
Number average molecular weight (MW): 2300
Polydispersion Q=MW/MN: 1.56
Anticoagulant activity (USP XXI): 30 U/mg,
AntiXa activity: 154 U/mg,
APTT activity: 19 U/mg,
(See FIG. III)

EXAMPLE III

A commercial heparin originating from bovine lungs was used as raw material with the following characteristics:
Anticoagulant activity USP XXI: 165 U/mg.
Uronic acid content: 33.2% o.d.b.
Sulfur content: 12% o.d.b.
Nitrogen content: 2.4% o.d.b.
Rotary power in aqueous solution ($\alpha$) $D^{20}$: +44,7°
Mean molecular weight: 16,000 Daltons 300 gr of sodium heparin are dissolved in 12 lts of distilled water. The solution is concentrated to half its original volume by ultrafiltration with an AMICON H-10 P3-2025 membrane and dialyzed with two volumes of distilled water by the same equipment. 59.7 gr of sodium chloride and 300 ml of a 7.5% solution of Benzethonium chloride are added to the rejection of the previous operation. The solution (S1) is extracted with a volume of 6.5 lts of a 7.5% solution of benzethonium chloride in dichloromethane previously equilibrated with a 0.17M sodium chloride aqueous solution. The phases are separated by extraction or centrifuging. The dichloromethane is transferred to a jacketed reactor with an agitator and 300 ml of pure benzyl chloride is gently mixed in at a temperature of 20° to 25°, maintaining agitation during 6 hours. After this operation, 10 ml of 1N hydrochloric acid are added and the solution is extracted with 6 lts of a 0.12N sodium chloride aqueous solution.

400 ml of 2N NaOH are added to the saline aqueous solution which is maintained in agitation during 2 hours at 4° C. and then neutralized with 1N HCl, dialyzed with an ultrafiltration membrane of 1000 NMW cut-off and lyophylized (P1).

100 ml of 2N sodium hydroxide are added to the aqueous saline solution containing the benzyl heparinate and maintained in gentle agitation for 2 hours at 4° C. The solution is then neutralized with 1N hydrochloric acid and dialyzed with an ultrafiltration membrane of 1000 NMW cut-off until the chlorides are eliminated. The rejected solution is lyophylized (P2). P1 and P2 are blended obtaining 273 gr of product with the following characteristics:
Mean molecular weight: 5600
Average molecular weight (MW): 6450
Number average molecular weight (NW): 4100
Polydispersion Q=MW/MN: 1.57
Anticoagulant activity (USP XXI): 73 U/mg.
AntiXa activity: 171 U/mg.
APTT activity: 64 U/mg.
(FIG. IV)

The oligosaccharide mixtures obtained by the process described in this invention have been chemically and biologically characterised.

Distribution of Molecular Weights

The molecular weight distribution was determined by high pressure liquid chromatography in TSK 2000 and TSK 3000 columns using Cl as the mobile phase. The elution profile was detected with the use of a UV (205 nm) detector.

FIG. V demonstrates the comparative distributions of the products obtained by: a) the process of this invention; b) depolymerization with nitrous acid; and c) b-elimination without fractionation. The results in FIG. 5 were obtained using HPLC.

In the first case, polydispersion is lower and even the mean molecular weights of (b) and (c) are apparently close (4800 and 5500), the contribution of high molecular weights is larger in (b) and (c) than in (a).

Consequently in (a), the contribution of molecular weight fractions higher than 7500 D, which potentiate the interaction of Cofactor II with thrombine, has been minimized.

Affinity chromatography on Sepharosa ATIII demonstrates that the compound obtained with the invention contains more than 27% of the composition that binds to the ATIII. The latter is the consequence of the selectivity of the initial treatment by phase partition, eliminating the fractions of low anionic density, characterized by the low ratio of the content in O-Sulfate, N-Sulfato to Carboxilic groups.

Assay of the Coagulation Parameters

AntiXa, antiIIa, TT and APTT in "in-vitro" treatment with blood from rabbits and dogs of the unfractioned heparin and oligosaccharide fractions, subject of this invention.

Inactivation of the Xa Factor

Animal: New Zealand rabbit.
Sex: Male
Treatment: Std. WHO 1 Low Molecular Weight Heparin (in vitro).
Assay: Chromogenic method antiXa KABI Coatest.

| ANTI Xa FACTOR ACTIVITY (Absorbances) | | | | | | |
|---|---|---|---|---|---|---|
| Animal | Concentration of substance assayed (UaXa/ml) | | | | | |
| No | 0.0 | 0.2 | 0.4 | 0.6 | 0.8 | 1.0 |
| 348 | 0.981 | 0.947 | 0.908 | 0.864 | 0.825 | 0.794 |
| 296 | 0.934 | 0.928 | 0.905 | 0.884 | 0.863 | 0.842 |
| 342 | 1.033 | 0.962 | 0.890 | 0.838 | 0.783 | 0.723 |
| 350 | 1.106 | 1.047 | 0.993 | 0.960 | 0.890 | 0.872 |
| 349 | 1.047 | 0.979 | 0.975 | 0.936 | 0.837 | 0.817 |
| MEDIA | 1.020 | 0.973 | 0.934 | 0.896 | 0.840 | 0.810 |
| D.E. | 0.0656 | 0.0456 | 0.0464 | 0.0506 | 0.0403 | 0.0564 |
| E.E.M. | 0.0293 | 0.0204 | 0.0208 | 0.0226 | 0.0180 | 0.0252 |
| DIRECT LINEAL REGRESSION | | | | | | |
| A = 1.0184    r = −0.9980 | | | | | | |
| B = −0.2124 | | | | | | |
| Treatment: H-BPM-B (in vitro) (Oligosaccharide fraction (Example II)) | | | | | | |
| 348 | — | 0.101 | 0.208 | 0.308 | 0.312 | 0.482 |
| 296 | — | 0.261 | 0.482 | 0.698 | 0.840 | 1.080 |
| 342 | — | 0.251 | 0.595 | 0.873 | 0.920 | 1.588 |
| 350 | — | 0.232 | 0.402 | 0.797 | 0.957 | 1.188 |
| 349 | — | −0.012 | 0.232 | 0.355 | 0.557 | 0.760 |
| MEDIA | — | 0.167 | 0.398 | 0.606 | 0.717 | 1.020 |
| D.E. | — | 0.1189 | 0.1478 | 0.2589 | 0.2755 | 0.4217 |
| E.E.M. | — | 0.0532 | 0.0661 | 0.1158 | 0.1232 | 0.1886 |
| DIRECT LINEAL REGRESSION | | | | | | |
| A = −0.0259    r = 0.9920 | | | | | | |

-continued

| ANTI Xa FACTOR ACTIVITY |
|---|
| (Absorbances) |

B = 1.0125

Animal: Beagle dog
Sex: Male
Treatment: H-BPM-B (in vitro) (Std. WHO I-LMWH)

| ANTI Xa FACTOR ACTIVITY | | | | | | |
|---|---|---|---|---|---|---|
| (Absorbances) | | | | | | |
| Animal | Concentration of substance assayed (UaXa/ml) | | | | | |
| No | 0.0 | 0.2 | 0.4 | 0.6 | 0.8 | 1.0 |
| 6HL6 | 1.143 | 0.977 | 0.780 | 0.684 | 0.567 | 0.489 |
| 6HQ3 | 1.202 | 1.063 | 0.822 | 0.714 | 0.597 | 0.493 |
| 6HQ4 | 1.171 | 0.986 | 0.780 | 0.646 | 0.541 | 0.450 |
| 6GK4 | 1.164 | 1.015 | 0.830 | 0.678 | 0.580 | 0.496 |
| 6HO4 | 1.219 | 0.963 | 0.818 | 0.642 | 0.542 | 0.439 |
| MEDIA | 1.180 | 1.001 | 0.806 | 0.673 | 0.565 | 0.473 |
| D.E. | 0.0305 | 0.0396 | 0.0241 | 0.0297 | 0.0243 | 0.0268 |
| E.E.M. | 0.0136 | 0.0177 | 0.0108 | 0.0133 | 0.0109 | 0.0120 |
| DIRECT LINEAL REGRESSION | | | | | | |

A = 1.1384  r = −0.9893
B = −0.7109

Treatment: H-BPM-B (invitro)
(Oligosaccharide fraction Example II))

| 6HL6 | — | 0.371 | 0.621 | 0.752 | 0.877 | 0.974 |
|---|---|---|---|---|---|---|
| 6HQ3 | — | 0.321 | 0.583 | 0.707 | 0.912 | 0.991 |
| 6HQ4 | — | 0.335 | 0.606 | 0.736 | 0.871 | 0.968 |
| 6GK4 | — | 0.362 | 0.568 | 0.729 | 0.880 | 0.960 |
| 6HO4 | — | 0.295 | 0.589 | 0.711 | 0.860 | 0.963 |
| MEDIA | — | 0.337 | 0.593 | 0.727 | 0.880 | 0.971 |
| D. E. | — | 0.0308 | 0.0206 | 0.0185 | 0.0195 | 0.0123 |
| E.E.M. | — | 0.0138 | 0.0092 | 0.0083 | 0.0087 | 0.0055 |
| DIRECT LINEAL REGRESSION | | | | | | |

A = 0.2351  r = 0.9839
B = 0.7775

The AntiXa Factor activites tested with dog and rabbit plasma are similar for the unfractioned heparin and the oligosaccharide fractions. FIGS. VI and VII.

Inhibition of IIa Factor

A chromogenic assay was performed with Coatest Kabi S.2238 Kit. Human plasma, poor in platelets and defibrinated was used for this assay. The following figure demonstrates the results obtained with unfractioned heparin (H) and an oligosaccharide fraction (H-BPM-B), the subject of this invention.

At the same concentration in plasma, a lower inhibition of thrombin is demonstrated for H-BPM-B. FIG. VIII.

THROMBIN TIME

The thrombin time, consisting of the time required for the plasma to generate thrombin has been determinated in plasma from rabbits and dogs. In both cases, substantial differences were observed between the unfractioned heparin and the oligosaccharides (H-BPM-B). For comparison purposes, two commercial depolymerized heparins (H-BPM-C and H-BPM-S) were analysed simultaneously with the oligosaccharides (H-BPM-B). FIGS. IX and X.
Animal: N.Z. rabbit
Sex: Male

| THROMBIN TIME (seconds) (MEAN VALUES) | | | | | | |
|---|---|---|---|---|---|---|
| | Concentration of substance assayed (U/ml) | | | | | |
| Treatment | 0.0 | 0.2 | 0.4 | 0.6 | 0.8 | 1.0 |
| H | 18.0 | 54.4 | 137.7 | >250 | >250 | >250 |
| H-BPM-B | 18.0 | 17.2 | 19.1 | 19.9 | 20.7 | 22.1 |
| H-BPM-S | 18.0 | 17.5 | 19.3 | 20.9 | 23.2 | 25.3 |
| H-BPM-C | 18.0 | 19.1 | 22.4 | 23.6 | 26.4 | 31.0 |

| STATISTICS ANALYSIS. | |
|---|---|
| 2 FACTORS WITH INTERACTION | |
| Between treatments, global level | $p < 0.001$ |
| H/H-BPM-B | $p < 0.001$ |
| H/H-BPM-S | $p < 0.001$ |
| H/H-BPM-C | $p < 0.001$ |
| H-BPM-B/H-BPM-S | NS |
| H-BPM-B/H-BPM-C | NS |
| H-BPM-S/H-BPM-C | NS |

Animal: Beagle dog
Sex: Male

| H | 9.9 | 19.6 | 52.5 | 116.0 | >250 | >250 |
|---|---|---|---|---|---|---|
| H-BPM-B | 9.9 | 10.1 | 10.5 | 10.7 | 11.4 | 11.8 |
| H-BPM-S | 9.9 | 10.2 | 10.8 | 11.9 | 12.7 | 13.8 |
| H-BPM-C | 9.9 | 10.7 | 11.8 | 13.0 | 14.5 | 16.6 |

| STATISTICS ANALYSIS. | |
|---|---|
| 2 FACTORS WITH INTERACTION | |
| Between treatments, global level | $p < 0.001$ |
| H/H-BPM-B | $p < 0.001$ |
| H/H-BPM-S | $p < 0.001$ |
| H/H-BPM-C | $p < 0.001$ |
| H-BPM-B/H-BPM-S | NS |
| H-BPM-B/H-BPM-C | NS |
| H-BPM-S/H-BPM-C | NS |

The following Tables show the thrombin Time for different concentrations of thrombin added to the plasma with various concentrations of glycosaminoglycans in plasma.

| THROMBIN TIME (sec) | |
|---|---|
| (thrombin = 6 U/ml) | |
| CONTROL | 5.5 |
| SUH (2 ug/ml) | 39.6 |
| SUH (1 ug/ml) | 11.4 |
| SUH (0.5 ug/ml) | 7.1 |
| Fraxiparine (42 ug/ml) | 5.5 |
| LMWH-B (2 ug/ml) | 5.5 |
| (thrombin = 4 U/ml) | |
| CONTROL | 6.4 |
| SUH (2 ug/ml) | 59.5 |
| Fraxiparine (2 ug/ml) | 8.8 |
| LMWH-B (2 ug/ml) | 8.3 |
| (thrombin = 2 U/ml) | |
| CONTROL | 11.2 ± 0.11 |
| Fraxiparine (4 ug/ml) | 92.8 ± 9.8 |
| N;WH-B (4 ug/ml) | 40.3 ± 4.2 |
| Fraxiparine (2 ug/ml) | 33.4 ± 0.8 |
| LMWH-B (2 ug/ml) | 22.8 ± 1.0 |
| Fraxiparine (1 ug/ml) | 16.6 ± 0.1 |
| LMWH-B (1 ug/ml) | 14.9 ± 0.2 |
| Fraxiparine (0.5 ug/ml) | 12.8 |
| LMWH-B (0.5 ug/ml) | 12.8 |

SUH: Commercial heparin
Fraxiparine ®: Depolymerized commercial heparin
LMWH-B: Oligosaccharide obtained with the invention.

There is no modification in the thrombin Time at high concentrations of thrombin inplasma referred to the control for depolymerized heparins However, the unfractioned heparin shows a considerable increase.

At lower concentrations of added thrombin and increasing the concentration of LMWH-B, there is a favorable difference compared with Fraxiparine which indicates for LMWH-B a possible lower risk of hemorrhage.

Activated Partial Thromboplastine Time (APTT)

Boehringer Mannheim's valuation kit was used with poor platelet plasma of dogs and rabbits. The subject (H-BPM-B) at various doses does not increase the APT time, contrary to the unfractioned heparin (H). FIG. XI,XII.

Animal: Beagle dog
Sex: Male

| ACTIVATED PARTIAL THROMBOPLASTINE TIME (sec) (Mean values) | | | | | | |
|---|---|---|---|---|---|---|
| | Concentration of substance assayed (U/ml) | | | | | |
| Treatment | 0.0 | 0.2 | 0.4 | 0.6 | 0.8 | 1.0 |
| H | 15.3 | 18.6 | 25.3 | 32.2 | 40.2 | 59.5 |
| H-BPM-B | 15.3 | 15.3 | 16.1 | 18.0 | 17.6 | 18.4 |

| STATISTICS ANALYSIS 2 FACTORS WITH INTERACTION | |
|---|---|
| Between treatments at global level | $p < 0.001$ |
| H/H-BPM-B | $p < 0.001$ |
| H/H-BPM-S | $p < 0.001$ |

Animal: New Zealand Rabbit
Sex: Male

| | | | | | | |
|---|---|---|---|---|---|---|
| H | 47.4 | 78.4 | 154.1 | 200.0 | 232.5 | >250 |
| H-BPM-B | 47.4 | 57.9 | 57.1 | 57.7 | 59.9 | 67.4 |

| STATISTICS ANALYSIS 2 FACTORS WITH INTERACTION | |
|---|---|
| Between treatments a global level | $p < 0.001$ |
| H/H-BPM-B | $p < 0.001$ |

Influence on the Platelet Aggregation

Numerous studies suggest that the hemorrhage effect of heparin is caused by its action on the platelet functions. Salzman et al (J. Clin. Invest., 65, 64, 1980) studied the influence of molecular weight on the interaction of heparin and platelets. They concluded that high molecular weight fractions (20,000) presented a higher reactivity than the low molecular weight fractions.

In the present study the antiaggregant activity of commercial heparin (H) and the subject of this invention (H-BPM-B) on rabbit washed platelets suspended on Tyrode was investigated. The platelet aggregation was provoked with a solution of collagen (100 mcg/ml) referred to a saline control. The study concluded that, for equal doses, the subject (H-BPM-B) presented a much lower effect on platelet aggregation than commercial heparin (H), and thus lower hemorrhage risk. FIG. XIII.

Evaluation of the Antithrombotic Activity "in Vivo" in Rats

The formation of thrombus was induced by ligature of the cava vein. Commercial heparin and the subject were administered in dosis of 200 UaXa/Kg. and 50-100 and 200 UaXa/kg. respectively, by subcutaneous injection (s.c.) and both were referred to a control. The results show equal activity for both, the subject and commercial heparin. when administered in equal doses. However, the subject presents a much lower anti-F IIa activity, in comparison to commercial heparin, resulting in a much lower risk of hemorrage with the same antithrombotic activity.

Influence on Bleeding Time

The influence on bleeding time was evaluated by the method of total tail transection. As shown on the table below, the results indicate a very significant reduction of bleeding time for the subject in comparison to commercial heparin.

| TREATMENT | Dose (UaXa/mg) | Bleeding Time (sec) |
|---|---|---|
| Control | — | 309 ± 20 |
| Com. Heparin | 240 | 764 ± 40 |
| Com. Heparin | 100 | 659 ± 41 |
| H-BPM-B | 50 | 327 ± 20 |
| H-BPM-B | 100 | 361 ± 40 |
| H-BPM-B | 240 | 446 ± 30 |

Influence on Human Platelet Factor 4 (PF4)

The PF4 is a physiological inhibitor of unfractioned heparin released by the platelets. The disappearance of human PF4 was studied in the rabbit after pre-treatment with standard unfractioned heparin (H) and the subject (H-BPM-B). Both were given i.v. and PF4 (60 mcg/kg) was given by the same route. Immunoreactive PF4, in untreated rabbits, disappeared very rapidly, while in the presence of H and H-BPM-B this process was slower. As observed in the table below, the results indicate that H-BPM-B has in vivo a good affinity for PF4, although less than H on a ponderal basis.

| | | PF4 kinetic parameters | |
|---|---|---|---|
| Treatment | Dose (mg/kg) | Co (mg/ml) | $t_{\frac{1}{2}}$(min) |
| Saline | — | 128.8 | 2.1 |
| H | 3.44 | 1055.4 | 13.9 |
| H | 0.86 | 776.2 | 7.2 |
| HBPMB | 0.86 | 457.6 | 3.4 |
| HBPMB | 3.44 | 831.7 | 5.6 |

Study of Toxicity

The toxicity of HBPMB was studied and the lethal dose 50 (LD 50) was calculated. The subject of the study was given i.v. and s.c. When administered intravenously, the subject was given in one dose at 10 ml/kg body weight, and the LD 50 was calculated to be 3,300 mg/kg. When a dose of 4,000 mg/kg was given, H-BPM-B induced neurological symptoms (clonic convulsions), due to the toxicity of mucopolysaccharides. When HBPMB was administered subcutaneously the LD 50 was calculated to be greater than 6,700 mg/kg.

The described product, given its characteristics and properties, results appropriate for the prophylaxis and treatment of thromboembolic diseases Moreover, the subject has a higher rate of benefits/haemorrhagic risk in comparison to unfractioned heparin in haemodialysis.

The low incidence of H-BPM-B in the APTT and the thrombin Time (TT), when given in the usual doses of 0.5-1.0 mg/kg. minimize biological control during application.

The product described is appropriate for the preparation of pyrogen-free pharmaceuticals, injectable intravenously and subcutaneously.

It is also possible to administer the product orally, as gastric-resistant capsules.

As a consequence of the low molecular weight of the product, it is fit for liposome-encapsulation for its controlled release intravenously, or its topical administration.

When the product is compared to unfractioned heparin in studies of bioavailability, performed subcutaneously in rats, the former shows 93% values, while the later shows 48-60%.

The studies done "in vitro" with human skin in a Franz difussion cell demonstrate the passage of 100% of activity of the subject. Therefore, the product could be formulated adequately for topical ointments, creams, as well as for other transdermal delivery systems (e.g. occlusive patches, microreservoirs, etc.) Furthermore, the subject could also be formulated for supositories and inhalators, and associated with venotonic agents or thrombolitics.

We claim:

1. A process for making an oligosaccharide fraction from heparin, said oligosaccharide fraction having antithrombotic activity, bioavailability, almost no toxic effects as well as a lower hemorrhagic risk and a reduction in bleeding time compared to commercial heparin, comprising the steps of:
    a. ultrafiltering an aqueous starting solution of said heparin through a membrane of 3,000 D nominal molecular weight cutoff to form a rejected ultrafiltered heparin solution from which molecular weight fractions of said heparin of less than 3,000 D are excluded so that said oligosaccharide fraction does not contain molecular fragments too short for binding with antithrombin and thrombin;
    b. performing a phase partitioning of the rejected ultrafiltered heparin solution with an aqueous saline solution and a solvent and forming a heparin-quaternary ammonium complex substantially soluble in said solvent, said phase partitioning and said forming resulting in a solvent phase and a saline phase, said phase partitioning being performed so as to eliminate heparin fractions having an anionicity which is so low as to provide approximately no specificity for said antithrombin from said oligosaccharide fraction;
    c. then depolymerizing the heparin-quaternary ammonium complex in said solvent phase;
    d. after said depolymerizing performing at least one other phase partitioning of said solvent phase with another aqueous saline solution to form another saline phase and another solvent phase;
    e. after said at least one other phase partitioning again forming said heparin-quaternary ammonium complex in said other solvent phase and depolymerizing said heparin-quaternary ammonium complex in said other solvent phase; and
    f. obtaining said oligosaccharide fraction having a defined molecular weight range of less than 5000 D at least from said other saline phase.

2. A process according to claim 1, wherein said solvent is dichloromethane.

3. A process according to claim 1, further comprising adding benzyl chloride to said solvent phase to benzylate said heparin-quaternary ammonium complex contained in said solvent phase, after said adding of said benzyl chloride adding benzyltrimethylammonium hydroxide to said solvent phase to form a depolymerized heparin fraction in said solvent phase and performing said other phase partitioning of said solvent phase by mixing said solvent phase with said other saline solution to form said other solvent phase and said other saline phase and obtaining one of said oligosaccharide fractions from said other saline phase.

4. A process according to claim 3, wherein said obtaining said one oligosaccharide fraction includes the steps of adding sodium hydroxide to said other saline phase, neutralizing said other saline phase, after neutralizing dialyzing and lyophilizing said other saline phase.

5. A process according to claim 3, further comprising the steps of adding an organic base to said other solvent phase, subsequently performing an additional one of said phase partitionings by mixing said other solvent phase with an additional saline solution to obtain an additional saline phase and adding sodium hydroxide solution to said additional saline phase.

6. A process according to claim 5, further comprising the steps of subsequently dialyzing and lyophilizing said additional saline phase to obtain another one of said oligosaccharide fractions.

7. A process according to claim 1, wherein said heparin is present in said aqueous starting solution in a concentration of from 1% to 10% by weight.

8. A process for making an oligosaccharide fraction made from heparin, said oligosaccharide fraction having antithrombotic activity, bioavailability and almost no toxic effects as well as a lower hemorrhagic risk and a reduction in bleeding time compared to commercial heparin and a molecular weight range of less than 5000 D, said process comprising the steps of:
    a. ultrafiltering an aqueous starting solution of said heparin through a membrane of 3,000 D nominal molecular weight cutoff to form a rejected ultrafiltered heparin solution from which molecular weight fractions of said heparin of less than 3,000 D are excluded so that said oligosaccharide fraction does not contain molecular fragments too short for binding with antithrombin and thrombin;
    b. performing a phase partitioning of the rejected ultrafiltered heparin solution with aqueous saline solution and dichloromethane and forming a heparin-quaternary ammonium complex to form a dichloromethane phase and a saline phase to eliminate heparin fractions having an anionicity which is so low as to provide approximately no specificity for said antithrombin from said oligosaccharide fraction, and
    c. adding benzyl chloride to said dichloromethane phase to benzylate said heparin-quaternary ammonium complex contained in said dichloromethane phase and after said adding of said benzyl chloride adding benzyltrimethylammonium hydroxide to said dichloromethane phase to form a depolymerized heparin fraction in said dichloromethane phase and subsequently isolating said oligosaccharide fraction by steps including another phase partitioning to form another saline phase, debenzylizing, adding sodium hydroxide to said other saline phase, neutralizing said saline phase and subsequently lyophilizing and dialyzing said other saline phase after said neutralizing.

* * * * *